(12) United States Patent
Einarsson (10) Patent No.: US 7,488,349 B2
(45) Date of Patent: Feb. 10, 2009

(54) VENTILATED PROSTHESIS SYSTEM

(75) Inventor: Palmi Einarsson, San Juan Capistrano, CA (US)

(73) Assignee: Ossur hf, Reykjavik (IS)

( * ) Notice: Subject to any disclaimer, the term of this patent is extended or adjusted under 35 U.S.C. 154(b) by 54 days.

(21) Appl. No.: 11/723,595

(22) Filed: Mar. 21, 2007

(65) Prior Publication Data

US 2007/0225824 A1 Sep. 27, 2007

Related U.S. Application Data

(60) Provisional application No. 60/785,344, filed on Mar. 24, 2006.

(51) Int. Cl.
*A61F 2/60* (2006.01)
(52) U.S. Cl. .......................................... 623/33; 623/32
(58) Field of Classification Search .............. 623/32–37
See application file for complete search history.

(56) References Cited

U.S. PATENT DOCUMENTS

| 52,964 | A | 3/1866 | Byrd |
| 701,318 | A | 6/1902 | Fenner et al. |
| 1,066,605 | A | 7/1913 | Hanger |
| 2,229,728 | A | 1/1941 | Eddels |
| 2,578,019 | A * | 12/1951 | Ryan ........................... 623/36 |
| 3,111,683 | A | 11/1963 | Bach |
| 4,842,608 | A | 6/1989 | Marx et al. |
| 4,872,879 | A | 10/1989 | Shamp |
| 5,480,455 | A | 1/1996 | Norvell |
| 5,529,575 | A | 6/1996 | Klotz |
| 5,653,766 | A | 8/1997 | Naser |
| 5,728,165 | A | 3/1998 | Brown |
| 5,888,231 | A | 3/1999 | Sandvig et al. |
| 6,991,657 | B1 | 1/2006 | Price |
| 2005/0149202 | A1* | 7/2005 | Schaffer et al. ............... 623/36 |
| 2006/0135900 | A1 | 6/2006 | Ingimundarson |

* cited by examiner

*Primary Examiner*—Bruce E Snow
(74) *Attorney, Agent, or Firm*—Bacon & Thomas, PLLC (57) ABSTRACT

A prosthesis system including a ventilated shell, and a substantially compliant, ventilated spacer element that defines a first surface having a frictional feature. The spacer element is arranged to secure to an internal surface of the shell. The prosthesis system also includes a connector that is secured to a distal end of the shell, and a retainer supported by the connector so as to extend into a cavity formed by the shell.

20 Claims, 4 Drawing Sheets

VENTILATED PROSTHESIS SYSTEM

CROSS REFERENCE TO RELATED APPLICATIONS

This application claims the benefit of priority of U.S. provisional application 60/785,344, filed on Mar. 24, 2006.

FIELD OF THE INVENTION

This invention relates to a ventilated prosthesis system for a residual limb.

BACKGROUND OF RELATED ART

Existing prosthetic sockets on residual limbs tend to be bulky and cumbersome to wear. They may also be difficult to don and make the residual limb uncomfortable when worn due to a lack of ventilation. Moreover, most prosthetic sockets are permanently formed, thereby not accounting for swelling of a residual limb. These sockets also require time to be constructed, and there are very few socket options for new amputees prior to receiving a socket after surgery.

It is desirable to provide a simplified and compact prosthesis system that overcomes the drawbacks over known prosthesis systems. Further, it is desirable to provide a prosthesis system that can be worn temporarily and adjusted accordingly.

SUMMARY

Embodiments of the present invention are directed to a prosthesis system that serves to ventilate a residual limb, provide adjustable settings, and is easy to don. Moreover, these embodiments provide a streamlined prosthesis system that is lightweight and has a slim profile. The prosthesis system may be worn without custom settings, and may further serve as a transition or temporary prosthesis socket system prior to a permanently fitted socket system of a more traditional type.

In accordance with one embodiment, the prosthesis system includes a ventilated shell forming anterior, lateral and medial portions, and a substantially compliant, ventilated spacer element that defines a first surface having a frictional feature. The spacer element serves as a buffer between the shell and the residual limb. The prosthesis system also includes a connector that is secured to a distal end of the shell. The connector has a proximal side defining a recess. A retainer is provided for insertion within the proximal side recess of the connector so as to extend into a cavity formed by the shell.

In another embodiment, the shell includes anterior and posterior shells. The anterior shell is secured to the connector, whereas the posterior shell is connected to the anterior shell by straps extending therebetween. The spacer element forms a tubular liner having a closed distal end and an open proximal end.

In yet another embodiment, the shell forms a definitive, custom fitted socket. Similarly, the spacer element forms a tubular liner having a closed distal end and an open proximal end.

Numerous variations of the components used in the prosthesis system are described more fully in the following description.

BRIEF DESCRIPTION OF THE DRAWINGS

These and other features, aspects, and advantages of the present invention will become better understood with regard to the following description, appended claims, and accompanying drawings.

DETAILED DESCRIPTION OF VARIOUS EMBODIMENTS

A. Overview

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. § 112, paragraph 6.

Some of the components described herein share similarities to components in pending U.S. application Ser. No. 11/312,337, incorporated herein by reference and belonging to the assignee of this disclosure.

B. Environment and Context of Embodiments

Numerous embodiments of the invention are provided for assisting a leg amputee with a ventilated prosthesis system. Embodiments of the invention may be configured for both above the knee and below the knee amputees. The components of the embodiments may be adapted for other limbs and anatomy.

Embodiments of the invention may be dimensioned to accommodate different types, shapes and sizes of amputated legs. In addition, embodiments are adjustable to compensate for varying degrees of swelling and variable conditions of a residual limb.

For explanatory purposes, the embodiments described herein are divided into sections which are denoted by general anatomical terms for the human body. These terms include dividing the prosthesis system into anterior and posterior sections by an anterior-posterior plane. The anterior-posterior plane generally corresponds to the coronal or frontal plane of a human leg. Each of the anterior and posterior sections is further divided about the center of the leg by a proximal-distal plane and a lateral-medial plane.

The anatomical terms described herein are not intended to detract from the normal understanding of such terms as readily understood by one of ordinary skill in the art of orthotics and prosthetics.

Figure 1:
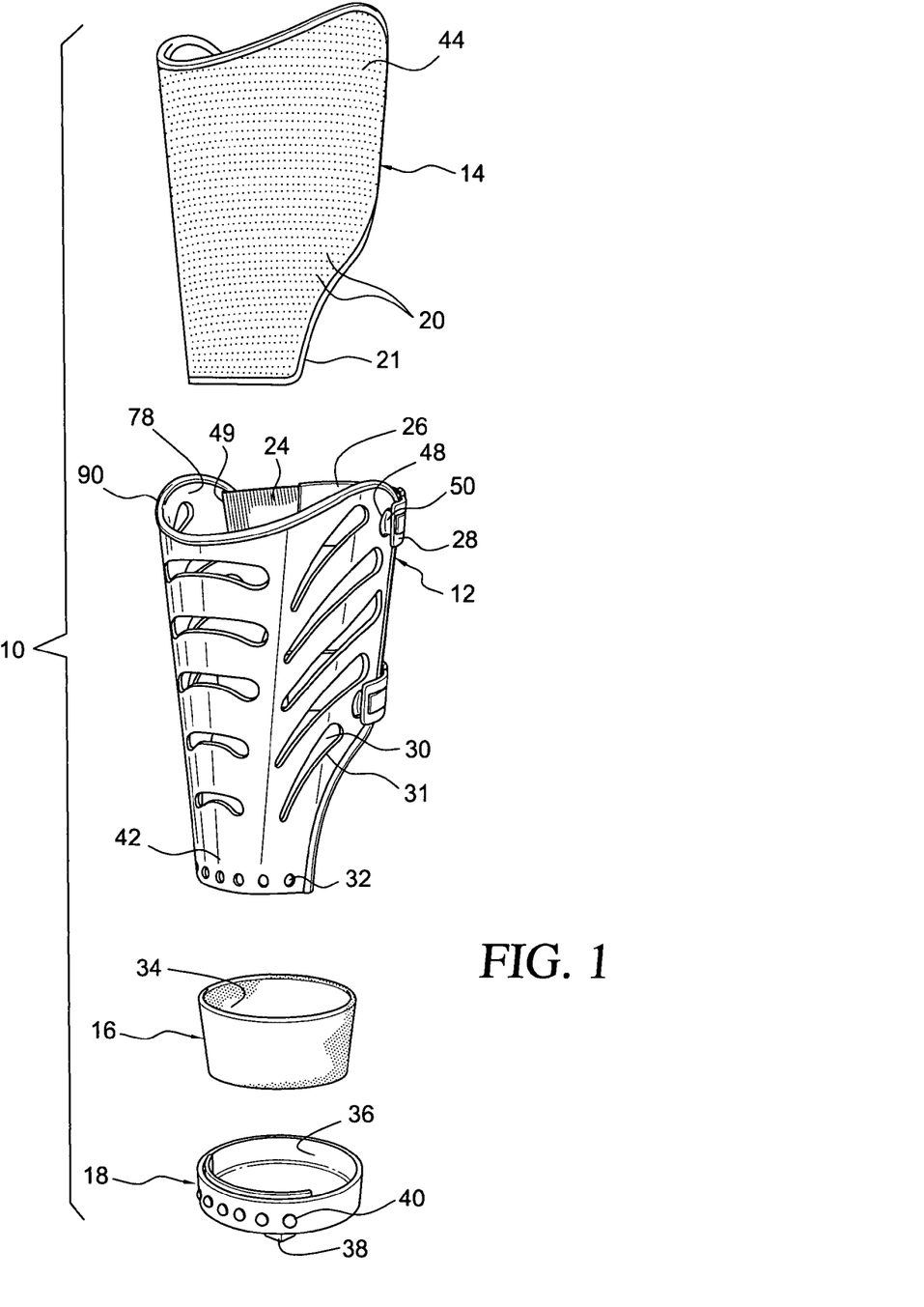
FIG. 1 is an exploded perspective view showing an embodiment of a ventilated prosthesis system according to the invention.
Figure 2:
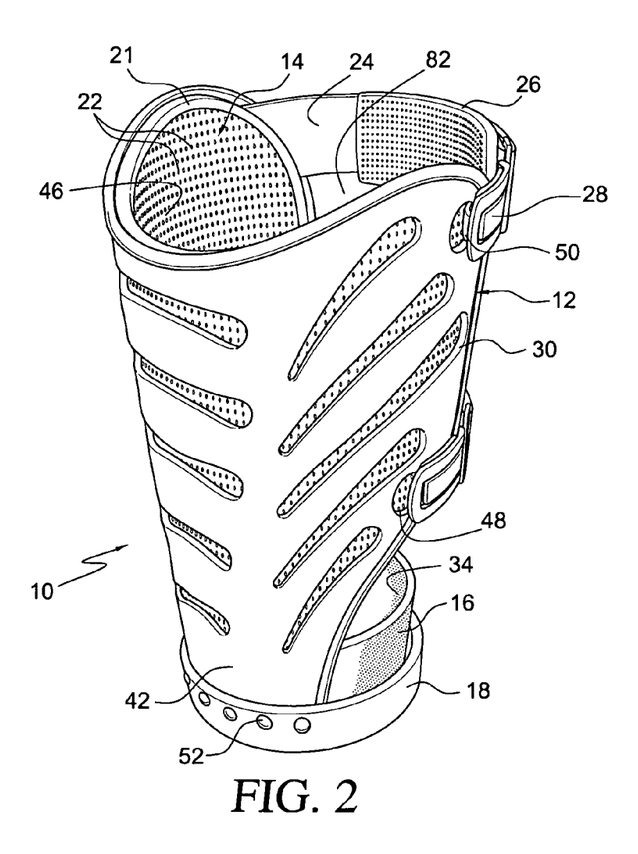
FIG. 2 is a perspective view showing the embodiment of FIG. 1.
Figure 3:
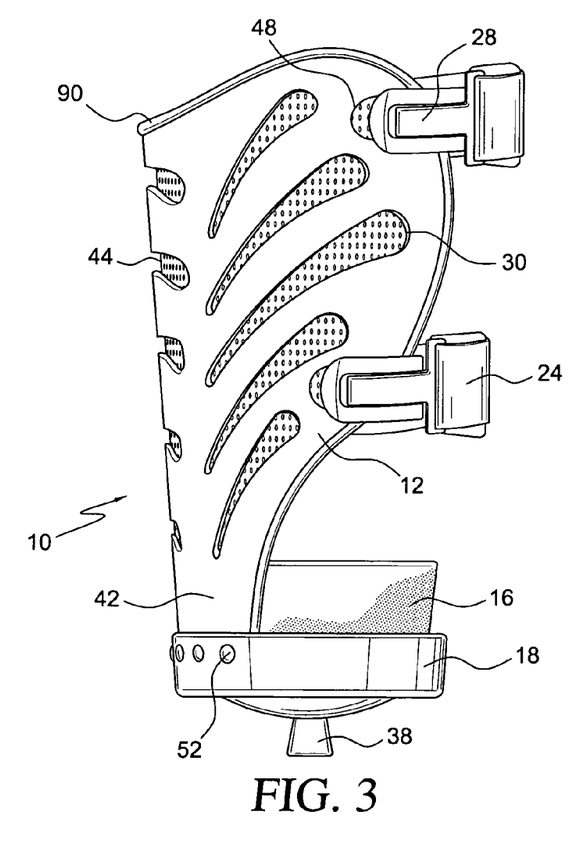
FIG. 3 is a side elevational view showing the embodiment of FIG. 1.

C. Various Embodiments of the Prosthesis System i. Overview of Prosthesis System Embodiments One embodiment of the prosthesis system according to the invention is shown in FIGS. 1-3. The prosthesis system 10 includes an anterior shell 12 having a cavity 82 that is adapted to receive a residual limb. A spacer element 14 is provided for location along an upper surface 78 of the shell 12, and is arranged to be intermediate of the residual limb and the shell 12. A connector 18 is attached to a distal end 42 of the shell 12. The connector 18 is arranged to receive a retainer 16 which extends into the cavity 82 of the shell 12. Suitable straps 24 are connected to the shell 12, particularly on medial and lateral sides thereof which are provided for securing the shell 12 to the residual limb.

Figure 4:
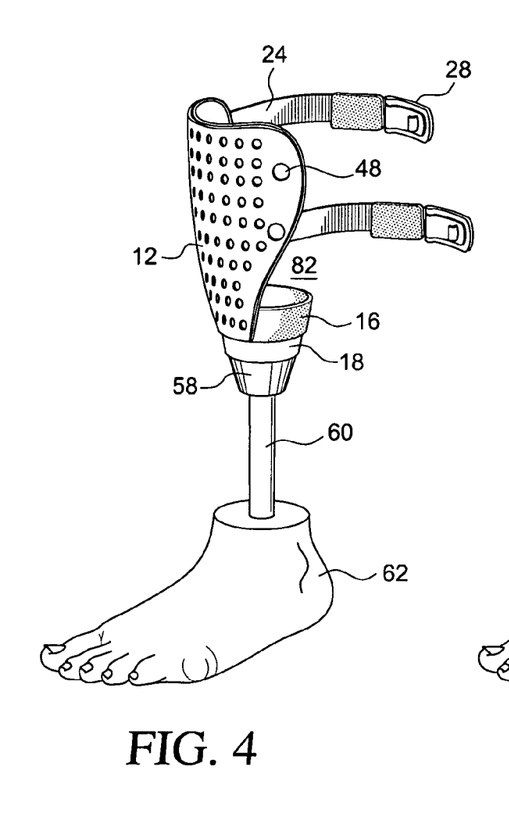
FIG. 4 is a perspective view showing another embodiment of a ventilated prosthesis system.
Figure 5:
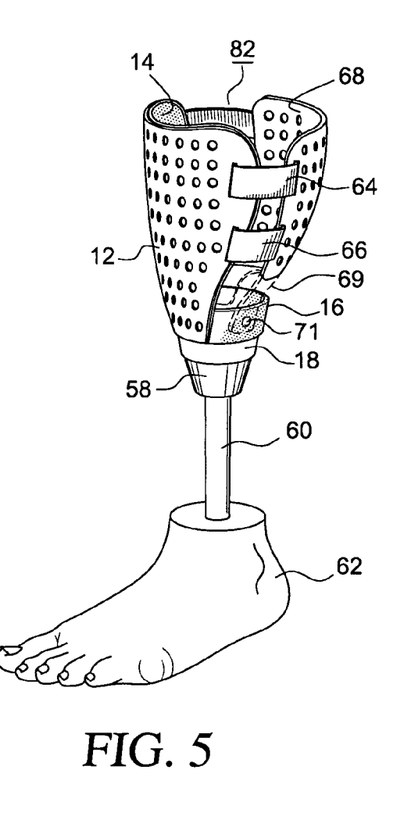
FIG. 5 is a perspective view showing yet another embodiment of a ventilated prosthesis system.

The ventilated prosthesis system 10 may be connected to a suitable prosthetic knee 58, pylon 60, and foot 62, as schematically depicted in FIGS. 4 and 5. It will be understood that one skilled in the art may connect other suitable components to the prosthesis system according to different applications While the foregoing embodiment has been described and shown, details as to different embodiments and variations of the components used therein will be described in more detail in the following discussion. Moreover, modifications of this embodiment and variations thereof will also be included in the following discussion. For example, the shell configuration and variations thereof may be used in applications that do not necessitate the connector, as in orthotic devices for securing limbs and other anatomy.

ii. Shells

FIGS. 1-3 illustrate one embodiment of the shell that may be used in the prosthesis system according to the invention. In this embodiment, the shell 12 is configured to cover portions of the anterior, lateral and medial sides of the residual limb. The shell of this embodiment may not, however, be configured to cover much, if any, of the posterior portion of the residual limb. This embodiment enables a user to tightly secure the shell onto the residual limb with the straps 24. This embodiment also enables the user to adjust the straps 24 according to different degrees of swelling the residual limb might undergo.

According to other embodiments, the shell may comprise a single part or multiple parts that surround portions of the both the anterior and posterior sides of the residual limb, or may define a socket having a similar construction that surrounds the residual limb in known prosthetic sockets, as described in U.S. Pat. Nos. 6,416,703 and 6,589,289, incorporated herein by reference and belonging to the assignee of this disclosure.

For example, FIG. 5 shows an embodiment of the shell 12 as forming an anterior shell and the shell 64 forming a posterior shell. These two opposing shells 12, 64 are connected by the straps 66. While the anterior shell 12 is preferably connected to the connector 18, as discussed below, the posterior shell 64 may be constrained by the straps 66 which connect to the anterior shell 12. The straps 66 may be shortened so as to reduce the cavity 82, and may further be elastic so as to draw the posterior shell 64 towards the anterior shell 12 when worn by a user with suitable adjustments.

In a variation of the embodiment of FIG. 5, the posterior shell 64 includes a lower segment 69 (shown in hidden lines) that extends to the connector 18. The lower segment 69 is shown as defining a cut-away section generally corresponding to a posterior portion of the connector 18 so as to permit rotation of the posterior shell 64 relative to the connector 18.

The lower segment 69 includes lateral and medial sides that connect to a pin or hinge device 71 secured to the connector 18. The pin or hinge device 71 allows the posterior shell 64 to be pivotally connected to the connector 18, and facilitates the donning of the anterior shell 12 and the posterior shell 68 on a residual limb by maintaining the connector, anterior and posterior shells together.

It will be understood that since the lower segment 69 of the posterior shell 64 is attached to the connector 18, a variation of this arrangement may include only the posterior shell 64 as being connected to the connector. It follows that the shell 12 itself is not directly secured to the connector and is only connected to the connector via the straps 66 linking it to the posterior shell 64.

Figure 6:
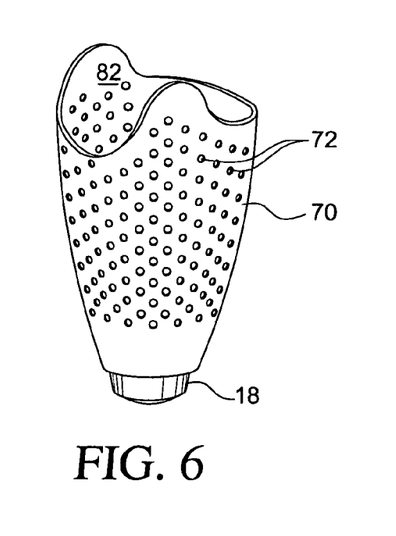
FIG. 6 is a perspective view showing an embodiment of a shell of FIG. 4.

Another embodiment is shown in FIG. 6 which includes a shell that effectively forms a definitive socket 70 which is of the type described in the aforementioned patents. This socket 70 includes a ventilation feature 72 that is generally uniformly formed and spaced in at least the proximal portion of the socket 70. The socket 70 is preferably formed to a general or specific the shape of a residual limb.

Returning to the basic embodiment of FIGS. 1-3, the shell 12 includes a ventilation feature 30. The ventilation feature 30 is defined by a plurality of slots 31 defined in a pattern. The slots 31 may include various shapes and sizes. In other variations, the ventilation feature 30 may be defined by any shape or size of opening that will provide a transfer of vapor and moisture from the residual limb through the shell 12.

Figure 7:
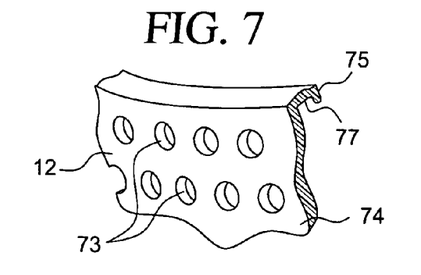
FIG. 7 is a sectional view showing an embodiment of the shell of FIG. 4.
Figure 8:
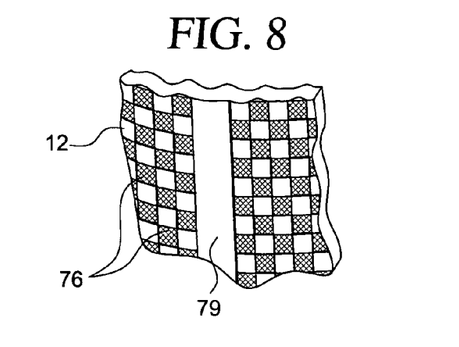
FIG. 8 is a sectional view showing a variation of the shell of FIG. 7.

Examples of other variations of the ventilation feature are shown in FIGS. 7 and 8. In each of these variations, the shell 12 may be provided with sections having only the ventilation feature, or the shell 12 in its entirety may have the ventilation feature. One variation is shown in FIG. 7, and by way of FIGS. 4-6, wherein the shell 70 has circular openings 73 that extend through the thickness of the shell body 74 thereof. The variation of FIG. 7 also exemplifies how the shell 12 may include a peripheral lip 75 that defines a groove 77 between the shell body 74 and the lip 75. The groove 77 is sized and configured to accommodate and retain a spacer element. The peripheral lip 75 may be provided in continuous or segments along the periphery of the shell 12.

Alternatively, the variation of FIG. 8 shows a grid or mesh configuration 76 that is finer in size than the openings 72 of FIGS. 4-6. The mesh configuration 76 may be continuous across the shell 12, or located at specific locations bordered with reinforcement sections 79 that provide additional structure and strength to the mesh configuration 76.

Referring again to the embodiment of FIGS. 1-3, the shell 12 includes appropriate openings 48, 49 appropriate for receiving detachable mounting brackets or buckles 28 for connecting the straps 24 to the shell 12. In addition, the shell 12 includes appropriate openings 32 for securing the connector 18 thereto.

The construction of the shell may be similar to the construction of the shells in U.S. patent application Ser. No. 11/312,337. For example, the shell 12 may include a compliant feature 90 located about the entirety or at least a portion about the periphery of the shell. The compliant feature provides a pressure-relieving flexible perimeter edge portion to the shell which accommodates sensitive skin and muscle areas of a wearer surrounding the shell.

The compliant feature 90 is preferably constructed of a material that is more flexible or softer than the material comprising the shell. The compliant feature 90 is arranged to extend beyond the outer perimeter of a main body of the shell, and is preferably a flexible resilient material that is secured to the shell by "overmolding," bonding, mechanical interlocking or any other suitable arrangement. An example of a method for providing the compliant feature is described in U.S. Pat. No. 5,445,602, incorporated herein by reference and belonging to the assignee of this disclosure.

In another example of the compliant feature, the shell may be constructed by a combination of rigid frame members with at least one flexible subshell having a compliant feature surrounding the periphery thereof. Exemplary materials that may be used for constructing the frame include metals such as aluminum, titanium, and steel, thermoset resin composite systems including glass or carbon fibers, and thermoplastics that have been rendered rigid by way of material composition and geometry of the frame members.

The sub-shell is substantially more flexible than the substantially rigid frame. While it is preferred that the rigid frame does not yield to the residual limb when worn, the sub-shell sufficiently is flexible so as to bend and conform to the residual limb. The rigid frame and flexible subshells may be configured in accordance with any of the shell embodiments described herein.

The compliant feature is distinguished from a main body portion in that it preferably has a softer texture. More specifically, the compliant feature has a hardness that is lower than the hardness of the main body. In one variation, the main body and the compliant feature are injection molded thermoplastics that are integrally molded together. An exemplary combination of materials comprises thermoplastic polyurethane elastomers sold under the name ELASTOLLAN by BASF group.

In any of the embodiments described herein, the shell may be custom sized and contoured to accommodate the leg of a particular wearer of the brace. Also, the shell may be preformed to curve to the contour of a residual limb, or curved as a result of the tension of the straps adjusted between lateral and medial sides of the shell. While the embodiment described herein assumes that the shell may be sufficiently flexible to accommodate a residual limb, the shell can also be configured to be substantially rigid. Whether the shell is configured for temporary and universal usage irrespective of a particular residual limb, or permanent usage for a particular limb, the stiffness of the shell may be arranged or modified accordingly.

The shell may be constructed of a variety of materials such as TRIAX (abs/nylon blend), polypropylene, polyethylene, nylon, carbon or glass fiber prepeg with thermosetting or thermoplastic resins, and rigid foam from EVA, platezote or polyurethane. In another variation, the proximal and distal shells may be constructed similarly to the orthotic sleeve described in U.S. Pat. No. 6,592,539, incorporated herein by reference and belonging to the assignee of this disclosure.

iii. Spacer Element

As shown in the embodiment of FIGS. 1-3, the spacer element 14 is contoured in a similar configuration to the shells 12. This spacer element 14 is arranged with a ventilation feature 20 so as to be breathable by permitting a free flow of air therethrough. The spacer element 14 preferably also includes a friction feature 22 on at least one side thereof.

This embodiment of the spacer element 14 is secured or merely worn or arranged adjacent to the rear surface of the shell 12. The spacer element may be connected to the shell via removable means, such as with a hook and loop fastener system, or may alternatively be secured to the shell via stitching, adhesives, or other similar fastener features. Alternatively, the spacer element may be retained by the shell via the grooves described in connection with the shell variation of FIG. 7. This embodiment of the spacer element is intended to provide sufficient frictional force to maintain the shell against the residual limb at least partly due to the straps 24 and the frictional feature.

In the embodiment of FIGS. 1-3, the ventilation feature 20 comprises a pattern of openings defined across the spacer element 14 between the borders 21 of the spacer element 14. Alternatively, the ventilation feature 20 may comprise a breathable fabric, and may be combined with a pattern of perforations to further enhance the breathability of the spacers. Further yet, the spacer element may be constructed from a material that provides cushioning and compresses, at least in part, when the prosthesis system is worn.

The friction feature 22 is preferably provided on least a rear surface 46 the spacer element 14. This friction feature 22 has a high frictional coefficient against the skin or clothing. Moreover, the friction feature 22 does not occlude the ventilation feature 20 of the spacer element 14, and permits a transfer of air through the spacer.

Alternatively, the friction feature 22 may be provided on both front and rear surfaces of the spacer. This particular variation enables the spacer element to frictionally engage the shell, and may be provided with additional securing means for engagement with the shell. In yet another alternative, the spacer element may be constructed of sections of elasticized fabric and coated on at least the rear surface with silicone of the type described in U.S. Pat. No. 6,592,539.

As shown in FIGS. 1-3, the spacer element 14 may have a mesh or core portion that permits the passage of air therethrough, and yet is compressible to provide adequate cushioning and securing to a residual limb when the prosthesis system is worn. In addition, the border 21 of the spacer element preferably includes a reinforced edging provided to protect the core portion, and enhance the durability of the spacer.

Preferred substrate materials that may be used to form a substrate for the spacer element include foams, neoprene, and textiles. While numerous materials may be used as the spacer material, it is desirable that these materials have a three-dimensional knit structure covered by a mesh that provides sufficient breathability, insulation, compression, durability, and recovery. An exemplary spacer material is a three-dimensional fabric produced by Gehring Textiles under product numbers SHR 701, SHR 714 or SHR 754F.

The rear surface of the spacer element may include the friction feature comprising a continuous, discrete layer of cured silicone composition. The silicone composition is preferably sufficiently thick and soft to be comfortable to the user, and provides a seal against the residual limb. The friction feature may have apertures which correspond to apertures of the mesh surface of the three-dimensional fabric when such a fabric is used to form the substrate of the spacer. In an alternate variation, the silicone coating may comprise a plurality of dots, lines or other discrete portions of suitable geometry which are deposited to the surface of the substrate forming the spacer.

The silicone composition may be mixed with scenting, anti-inflammatory, anti-bacterial, and coloring agents. Moreover, the silicone composition may include skin friendly agents such as aloe vera or Vaseline. A more complete description of additives to the silicone may be found in U.S. Pat. No. 6,485,776, incorporated herein by reference and belonging to the assignee of this disclosure.

The silicone composition preferably has a Shore hardness of 25-70; a minimum tensile strength of 230 lbs/inch; a 100% modulus of 8 psi; a 500% modulus of 61 psi; a minimum tear strength of 49 lbs/inch; a maximum strength of 500 lbs/inch and an elongation of about 1000%.

It will be noted that the friction feature may comprise a variety of materials in addition to silicone. Such materials include those having frictional features which may be skin-friendly, and can be laminated, bonded or coated onto a substrate to form the spacer.

The friction feature may be disposed in a uniform thickness in both circumferential and longitudinal directions, or may have a varying thickness to accommodate varying shapes of a leg, protrusions, contours, etc. The friction feature can also be configured to have a specific relief from localized pressure that may result from installation spacer element on a residual limb.

Figure 9:
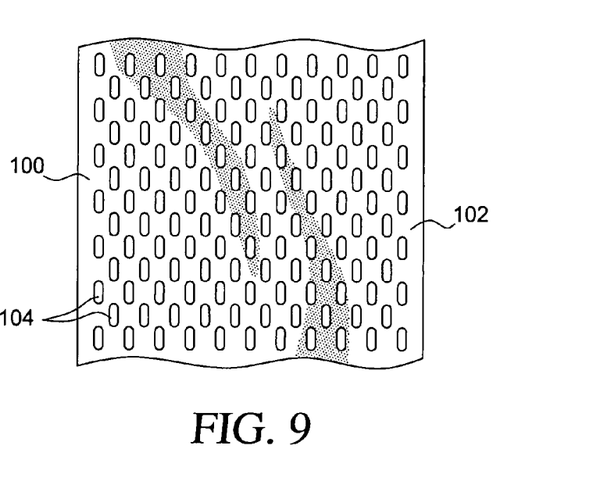
FIG. 9 is a sectional plan view showing an embodiment of the spacer element construction.
Figure 10:
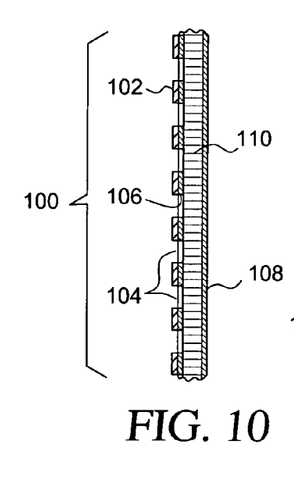
FIG. 10 is a sectional elevational view showing a cross-sectional variation of the spacer element construction of FIG. 9.

An example of a possible configuration of the spacer element is provided in FIGS. 9 and 10. FIG. 9 shows a surface of the spacer element 100 having a friction feature 102 with a plurality of apertures 104. FIG. 10 shows the spacer element having a spacer material comprising a three-dimensional fabric having a plurality of filaments 110 bounded by fabric surfaces 106, 108. The frictional feature 102 corresponds to non-apertured surfaces of the fabric surface 106, thereby defining holes 104.

In another variation (not shown), the spacer element does not include a friction feature. This spacer element would merely provide a compressive buffer between the shell and the residual limb. In yet another variation, the spacer element may comprise a textile having superior frictional properties, and as a result, merely the compression of the textile is sufficient to frictionally secure the spacer element against the residual limb.

In yet another variation, the spacer element may comprise a silicone mesh comprising a textile that is impregnated with silicone. This silicone mesh defines a pattern of apertures that permit the transport of air therethrough. In yet another variation, the spacer element is formed from a silicone sheet having a pattern of apertures, and sufficient thickness to serve as a buffer between the residual limb and the shell.

The spacer element 14 is not limited to the configuration of FIGS. 1-3. On the contrary, the spacer element 14 may form a tubular liner that surrounds the entirety of the leg, as in a silicone liner described in U.S. Pat. No. 6,136,039, incorporated by reference and belonging to the assignee of this disclosure. Such a liner may be tubular having open ends or a closed distal end for use with the anterior and posterior shells 12, 64 shown in the embodiment of FIG. 5, or the socket 70 in the embodiment of FIG. 6.

Figure 11:
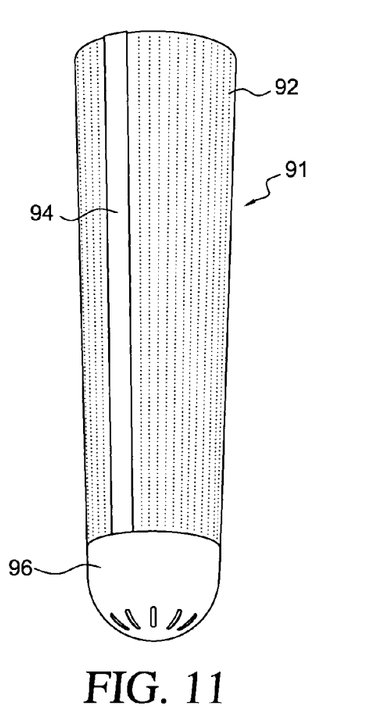
FIG. 11 is a perspective view showing an embodiment of a spacer element in tubular form.

FIG. 11 depicts an embodiment of a tubular liner 91 having an open end and a closed end. The general geometry of this liner is described in U.S. Pat. No. 6,136,039 and understood by those skilled in the art as a suspension liner for residual limbs. More specifically, the tubular spacer element 91 includes a spacer material 92 that is apertured and includes a friction feature on the inner surface (not shown), similar to the construction shown in FIGS. 9 and 10. The tubular spacer element 91 includes at least one elongate rib 94 extending from a distal base portion 96 adapted for mating with the connector. The rib 94 serves in part to provide structural support to the spacer material 92, and may cover any seam. In a variation, a plurality of spaced elongate ribs may be provided about the spacer material 92.

iv. Connector

In the embodiment shown in FIGS. 1-3, the connector 18 is arranged with a recess 36 for receiving the retainer 16. The connector 38 includes a pin 38 for connection to a corresponding adaptor locating on a prosthetic knee, prosthetic foot, pylon or other suitable prosthetic device.

The connector 18 has a means for connecting to the shell 12. According to the embodiment shown in FIGS. 1-3, the connector 18 includes a plurality of pins or buttons 40 which extend about the outer periphery thereof. These buttons 40 are adapted to extend through the openings 32 of the shell 12. While there are various ways of securing the buttons 40 to the shell 12, some examples include forming the openings 32 so that the buttons 40 interlock with the shell 12, or alternatively the buttons 40 are resiliently urged through the openings and secured therewith. This requires the shell 12 or the buttons 40 to be sufficiently resilient to permit the buttons 38 to compliantly pass through the openings 32.

Other suitable means may be used to connect the shell to the connector. Such means may include bonding the shell to the connector such that the distal portion of the shell forms a ring which encircles the connector. Alternatively, the connector may be integrally formed with the shell.

While in the embodiment of FIGS. 1-3 the connector 18 has a recess 36, the connector may be provided without the recess 36. Accordingly, suitable connecting pin(s) may be used, such as those known to skilled artisans in the field of prosthetics, to interlock with a corresponding adaptor on the retainer 16. Such known methods for connecting prosthetic devices include pyramid and socket adaptors, and clamps.

The connector 18 may be constructed from any suitable material understood by those skilled in the art to be used in typical adapters for prosthetic devices. Such materials include rigid plastics, steel, aluminum and titanium alloys, carbon fiber or other fiber composites, and combinations thereof.

v. Retainer

In the embodiment shown in FIGS. 1-3, the retainer 16 is configured for placement within the recess 36 of the connector 18. The retainer 16 has a generally concave surface 34 which is disposed within the cavity 82 of the shell 12. The retainer 16 is shaped and dimensioned to follow the contour of the distal end 42 of the shell 12.

The concave surface 34 is preferably contoured to accommodate the distal end of a residual limb. The concave surface 34 can also be configured in other shapes or may be formed of a custom shape for the residual limb.

The retainer 16 is supportive of the weight of the user of the ventilated prosthesis system 10. This variation of the retainer 16 is preferably constructed of a silicone elastomer that is of sufficient thickness to sustain its shape upon supporting the residual limb. As with the silicone-based frictional feature 22 of the spacer element 14, the retainer may include additives such as aloe vera and petroleum jelly in order to provide skin treatment qualities.

In other variations, the retainer 16 may be constructed from materials such as plastics or composite fiber systems. Alternatively, the retainer 16 may comprise foam, rubber or other suitable materials.

As indicated above, the retainer 16 may be configured so that it is attached to the connector 18. The retainer 16 may be modified to include suitable connecting means to secure it against the connector.

vi. Straps

In the embodiment of FIGS. 1-3, straps 24 are used to secure the ventilated prosthesis system to the residual limb. The straps 24 may be elastic, substantially elastic or inelastic. Tightening means may be used to secure the length of the strap, and maintain the length of the strap when the prosthesis system 10 is worn.

Regarding this embodiment, each of the straps 24 includes a cushion feature 26, such as foam or a textile pad that is secured thereon for enhanced rotational prevention and additional comfort. The straps each have an adjustment feature (not shown), such as a hook and loop fastener system, to enable adjustment of the length of such straps. Moreover, the cushion feature may include a frictional feature (not shown), such as a pattern of deposited silicone, rubber, or a mildly abrasive material. In addition, the cushion feature may be breathable, and have a construction similar to the spacers.

In one variation, the straps may be releasably secured to the knee brace. For example, the straps may include a snap fastener element that corresponds to a snap fastener element supported by shell of the prosthesis system. In another variation, other suitable releasable fasteners may be used to permit installation and removal of the straps from the shell.

Turning to the embodiment of FIG. 5 wherein the shell 12 includes anterior and posterior portions 12, 64, the straps 66 are mounted on opposed sides of the shells 12, 64 thereby forming a clamshell with the shells 12, 64. These straps 66 may be substantially elastic in order to draw the posterior shell 64 towards the anterior shell 12, or alternatively be substantially inelastic in order to prevent gradual extension of the straps as the prosthesis system is worn.

In variations, the straps 24 may be secured to the shell 12 in any of the ways described in U.S. patent application Ser. No. 11/312,330. Such straps may also have suitable tightening means that permit incremental adjustment, such as any of those described in Ser. No. 11/312,330.

vii. Other Embodiments

The various embodiments and the variations thereof described above in accordance with the prosthesis system of the present invention presents an amputee a comfortable and ventilated alternative to known prosthesis systems. The inventive prosthesis system is lightweight and has a streamlined profile that is simple to use for wearers of the system of various age groups. Patient comfort is also enhanced and donning and doffing of the system is eased with the novel features of the present prosthesis system. Versatility is also obtained since a single prosthesis system according to the invention may be sized and configured to a accommodate a variety of residual limbs with necessitating custom sizing of the system's components.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various components from different embodiments described herein. In addition to the variations described herein, other known equivalents for each feature can be mixed and matched by one of ordinary skill in this art to construct a prosthesis system in accordance with principles of the present invention. Moreover, the embodiments and components thereof described herein are not limited for use in prosthetic systems, but may be adapted to orthopedic systems for securing, supporting or comforting limbs or other anatomy.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

I claim:

1. A prosthesis system comprising:
   a ventilated shell having at least an inner surface;
   a substantially compliant, ventilated spacer element adjacent to the shell and defining a first surface having a frictional feature, the spacer element including a section corresponding to the inner surface of the shell;
   a connector secured to a distal end of the shell, the connector having a proximal side defining a recess; and
   a retainer provided within the proximal side recess of the connector, the retainer being generally cylindrical and having a concaved recess formed at a proximal end thereof.

2. The prosthesis system according to claim 1, wherein the spacer element has a spacer material including a three-dimensional fabric.

3. The prosthesis system according to claim 1, wherein the spacer element is releasably secured to the shell.

4. The prosthesis system according to claim 1, wherein the frictional feature is a continuous layer of a silicone composition.

5. The prosthesis system according to claim 1, wherein the first surface of the spacer element includes a plurality of apertures, the frictional feature defining apertures corresponding to the first surface apertures of the spacer element.

6. The prosthesis system according to claim 1, wherein the shell includes a plurality of through-extending openings.

7. The prosthesis system according to claim 1, further comprising a stability strap connecting to lateral and medial sides of the shell, and generally spanning a posterior side of the shell.

8. The prosthesis system according to claim 7, wherein the stability strap is attached to a buckle assembly releasably connected to one of the lateral and medial sides of the shell.

9. The prosthesis system according to claim 1, wherein the spacer element generally is a tubular liner defining an open end and a closed-end, an inner surface of the tubular liner having the friction feature disposed thereon.

10. The prosthesis system according to claim 9, wherein the tubular liner includes at least one elongate rib extending along an outer surface of the tubular liner.

11. The prosthesis system according to claim 10, wherein the spacer element comprises a breathable substrate having opposed first and second surfaces, the frictional feature being a silicone composition generally extending across at least one of the first and second surfaces in a manner so as to permit ventilation through the breathable fabric.

12. A prosthesis system comprising:
a ventilated shell having at least an inner surface;
a substantially compliant, ventilated spacer element adjacent to the shell and defining a first surface having a frictional feature, the spacer element including a section corresponding to the inner surface of the shell;
a connector secured to a distal end of the shell, the connector having a proximal side defining a recess; and
a retainer provided within the proximal side recess of the connector;
wherein the shell includes a lip defining a groove between the lip and the inner surface, the groove arranged and sized to retain the spacer element relative to the shell.

13. The prosthesis system according to claim 12, wherein the spacer element has a spacer material including a three-dimensional fabric.

14. The prosthesis system according to claim 12, wherein the frictional feature is a continuous layer of a silicone composition.

15. The prosthesis system according to claim 12, wherein the first surface of the spacer element includes a plurality of apertures, the frictional feature defining apertures corresponding to the first surface apertures of the spacer element.

16. The prosthesis system according to claim 12, wherein the shell includes a plurality of through-extending openings.

17. The prosthesis system according to claim 12, further comprising a stability strap connecting to lateral and medial sides of the shell, and generally spanning a posterior side of the shell, wherein the stability strap is attached to a buckle assembly releasably connected to one of the lateral and medial sides of the shell.

18. The prosthesis system according to claim 12, wherein the spacer element generally is a tubular liner defining an open end and a closed-end, an inner surface of the tubular liner having the friction feature disposed thereon.

19. The prosthesis system according to claim 12, wherein the tubular liner includes at least one elongate rib extending along an outer surface of the tubular liner.

20. The prosthesis system according to claim 19, wherein the spacer element comprises a breathable substrate having opposed first and second surfaces, the frictional feature being a silicone composition generally extending across at least one of the first and second surfaces in a manner so as to permit ventilation through the breathable fabric.

* * * * *